United States Patent
Liu et al.

(10) Patent No.: US 11,872,213 B2
(45) Date of Patent: Jan. 16, 2024

(54) FORMULATIONS

(71) Applicant: Glaukos Corporation, San Clemente, CA (US)

(72) Inventors: Xiaojun Michael Liu, Lake Forest, CA (US); James Jane-Guo Shiah, Irvine, CA (US); Gabriella Szekely, Irvine, CA (US)

(73) Assignee: Glaukos Corporation, Mission Viejo, CA (US)

( * ) Notice: Subject to any disclaimer, the term of this patent is extended or adjusted under 35 U.S.C. 154(b) by 0 days.

(21) Appl. No.: 17/587,510

(22) Filed: Jan. 28, 2022

(65) Prior Publication Data

US 2022/0233506 A1    Jul. 28, 2022

Related U.S. Application Data

(60) Provisional application No. 63/142,889, filed on Jan. 28, 2021.

(51) Int. Cl.
| | |
|---|---|
| *A61K 31/4178* | (2006.01) |
| *A61K 9/06* | (2006.01) |
| *A61K 9/00* | (2006.01) |
| *A61K 47/02* | (2006.01) |
| *A61K 47/12* | (2006.01) |
| *A61K 38/13* | (2006.01) |
| *A61K 31/46* | (2006.01) |
| *A61K 31/498* | (2006.01) |
| *A61K 31/56* | (2006.01) |
| *A61K 31/27* | (2006.01) |
| *A61K 31/5575* | (2006.01) |

(52) U.S. Cl.
CPC ........ *A61K 31/4178* (2013.01); *A61K 9/0048* (2013.01); *A61K 9/06* (2013.01); *A61K 31/27* (2013.01); *A61K 31/46* (2013.01); *A61K 31/498* (2013.01); *A61K 31/5575* (2013.01); *A61K 31/56* (2013.01); *A61K 38/13* (2013.01); *A61K 47/02* (2013.01); *A61K 47/12* (2013.01)

(58) Field of Classification Search
CPC .................................................. A61K 31/4178
See application file for complete search history.

(56) References Cited

U.S. PATENT DOCUMENTS

2015/0174211 A1*  6/2015  Nanduri ............... A61K 8/4953
                                                     514/263.34

OTHER PUBLICATIONS

International Preliminary Report on Patentability entered in PCT/US2022/014317, dated Apr. 12, 2022.

* cited by examiner

*Primary Examiner* — Nizal S Chandrakumar
(74) *Attorney, Agent, or Firm* — K&L Gates LLP

(57) ABSTRACT

Described herein are formulations including pharmaceutical agents comprising ester and/or lactone ring structures, and methods of using the same. The invention is also directed to a method and ophthalmic pharmaceutical compositions including solution and semisolid dosage forms (i.e. ophthalmic creams, gels, lotions, serums, and/or ointments) of treating a patient with various ocular diseases including presbyopia and dry eyes. The method comprising instructing a patient to apply one strip of the ophthalmic composition to the eyelids that includes pilocarpine or other active pharmaceutical ingredients containing ester and/or lactone ring structures with and without the buffering system.

11 Claims, 4 Drawing Sheets

FORMULATIONS

CROSS REFERENCE TO RELATED APPLICATION

This application claims the benefit of U.S. provisional patent application No. 63/142,889, filed Jan. 28, 2021, the entire disclosure of which is incorporated herein by reference.

FIELD

Described herein are compositions including pharmaceutical agents comprising ester and/or lactone ring structures, in sustained-release solid, semi-solid (gel, lotion, cream or ointment) formulations for topical and ophthalmic applications and methods of using the same.

SUMMARY

Described herein are compositions/formulations and processes for stabilizing active pharmaceutical ingredients including an ester and/or lactone ring structure in a liquid, semi-solid or solid composition. Methods of using these compositions in ophthalmic applications are also described. In some embodiments, the compositions described herein are considered stable chemically and physically. In some embodiments, that stability is when the compositions are being stored at room temperature.

Development of any pharmaceutical drug product must provide a composition that can maintain both physical and chemical stabilities in order to achieve a stable, scalable, safe, efficacious, and robust pharmaceutical product. The compositions and processes described herein can achieve this end. In some embodiments, the physical stability is achieved at lower pH such as 3.5 while maintaining chemical stability when the compositions are being stored at room temperature.

In some embodiments, described herein are selections of active pharmaceutical ingredient (API) free based as well as salt forms that can achieve control over chemical hydrolysis and/or oxidation.

In some embodiments, described herein are approaches to controlling chemical hydrolysis. These approaches can be applied alone (such as API stabilizer) or in combination (such as API stabilizers plus pH control) to achieve drug products with desirable properties.

In some embodiments, selection of pH buffers that can be used alone, as dual buffers, or as triple buffers to maintain high product quality and desirable physical and chemical stability are described.

In some embodiments, selection of charged low molecular weight peptides or amino acids (i.e. arginine, lysine, or histidine) or acidic amino acids (i.e. glutamate and aspartate) that can be used alone, or in combination with buffers to maintain high product quality and desirable physical stability and chemical stability are described.

In some embodiments, selection of one or more stabilizers can allow use with other active pharmaceutical ingredients that can form physical conjugates or complexes to achieve chemical stability.

In some embodiments, the API is added to a composition at a particular time to optimize formulation.

In some embodiments, described are drug compositions and compounding processes that occur at a controlled pH without use of any pH adjusters such as NaOH or HCl.

In some embodiments, described herein are compositions that are physically stable as semi-solids with conventional thickening agents at pH values favorable for API stability but, would otherwise have sub-optimal viscosity when compounded using common acid/base pH adjusters.

The present compositions and processes can be applicable to similar APIs that contain the same or similar chemical functional groups.

In some embodiments, described are compositions including: a pharmaceutical agent including an ester, a lactone ring, or an ester and a lactone ring, and a buffer, a stabilizer, or a combination thereof, wherein the composition is at a pH of between about 3.0 and 8.0.

The buffer can be a citrate buffer, acetate buffer, a glycolic acid buffer, a borate buffer, or a combination thereof. The stabilizer can be lactic acid, ascorbic acid, azeliac acid, or a combination thereof. In some embodiments, the composition can further include a Lewis acid, such as, $MgCl_2$ or $CaCl_2$.

In some embodiments, the pharmaceutical agent is pilocarpine. Pilocarpine can be provided as a free base, as an HCl salt, nitrate salt, or a combination thereof.

In some embodiments, the composition can include a thickener or thickeners, such as Sepineo P600 and cellulosic derivatives including hydroxypropyl cellulose (HPC), hydroxypropyl methylcellulose (HPMC), methyl cellulose (MC), hydroxyl ethyl cellulose (HEC), ethyl cellulose (EC), carboxylmethyl cellulose (CMC), and polysaccharides such as hyaluronic acid, carrageenan.

In some embodiments, the composition can have a pH of about 3.0 or about 5.5.

Other embodiments describe methods of producing a stable composition including a pharmaceutical agent. The methods can comprise mixing the pharmaceutical agent and other excipients in an aqueous medium to form a mixture and neutralizing the mixture to form the stabilized composition.

In some embodiments, the other excipients can include a buffer, stabilizer, an amino acid, a Lewis acid, or a combination thereof.

The pharmaceutical agent can include an ester, a lactone ring, or an ester and a lactone ring. In one embodiment, the pharmaceutical agent is atropine, travoprost or pilocarpine which can be provided as a free base or as a salt.

In some embodiments, the post neutralization can provide a pH of between about 3.0 and about 7.8, such as about 3.5 or about 5.5.

DETAILED DESCRIPTION

Figure 1:
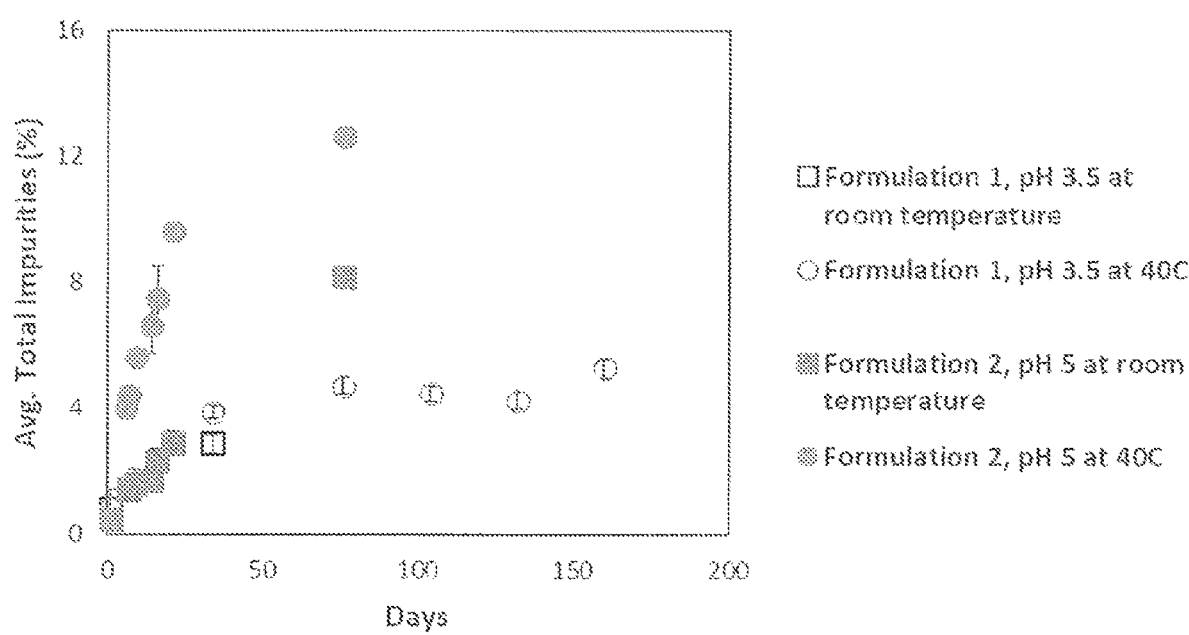
FIG. 1: Averaged total impurities (%) of Formulation 1 and 2 that were compounded with/by the same compositions, equipment, and processes. (□) represents Formulation 1 at pH 3.5 and stored at controlled room temperature, (○) represents Formulation 1 at pH 3.5 and stored at 40° C./75% RH, (■) represents Formulation 2 at pH 5.0 and stored at controlled room temperature, and (●) represents Formulation 2 at pH 5.0 and stored at 40° C./75% RH. There were n=3 at each sampling time points.

Described herein are formulations/compositions and processes for stabilizing active pharmaceutical ingredients that include an ester and/or lactone ring structure. The compositions can be in a liquid, semi-solid or solid composition.

In some embodiments, that stability can be characteristic of retaining activity when being stored at room temperature. In some embodiments, stability can be characterized as a lack of degradation products in a composition, for example, when stored at room temperature.

In some embodiments, stable state or stability when stored at room temperature can mean that a composition retains greater than about 60%, greater than about 70%, greater than about 80%, greater than about 90%, greater than about 95%, greater than about 96%, greater than about 97%, greater than about 98%, or greater than about 99% of its activity for greater than about a week, greater than about two weeks, greater than about four weeks, greater than about eight weeks, greater than about 12 weeks, greater than about six months, greater than about one year, or greater than about two years.

Active pharmaceutical ingredients (APIs) are typically added to drug compositions during the early compounding process to meet drug product quality requirements. APIs containing an ester bond or cyclic internal ester, lactone ring, such as Atropine and Pilocarpine, can be susceptible to acid or base catalyzed hydrolysis of the ester bond or lactone ring structure during the composition compounding process. The formation of the corresponding carboxylic acid and alcohol can lead to significant increases in impurities and shorten drug product shelf-life. The acid and base-catalyzed degradation can be highly influenced by the concentration of reagents present in the reaction in aqueous solutions and in solid or semi-solid compositions. Therefore, ester- and lactone-based drugs can be formulated at a pH optimal for their chemical stability using buffered systems and/or need to be stored under refrigeration.

For solid and semi-solid compositions, the physicochemical properties, such as viscosity and phase homogeneity, in addition to the chemical stability of a pharmaceutical product, are also critical. In some embodiments, pilocarpine HCl can achieve desirable viscosity and physical stability when formulated in a cream or gel dosage form with a thickener(s) or viscosity modulator (such as Carbopol®) that requires pH of about or greater than 5.0 for optimal viscosity. However, this pH range (about pH 5) of the composition can result in undesirably high hydrolytic degradation of pilocarpine. As shown herein, a correlation exists between API degradation and composition pH. In contrast, pilocarpine can be much more stable in a composition at pH of about or below 4. However, at this low pH range, the thickener's performance may not be optimal. Thus, desirable physicochemical properties and stability including viscosity may be difficult to attain.

Described herein are compositions, such as but not limited to potential compositions and a selection of aqueous media/API stabilizers that can improve the API stability. Further described are methods to achieve chemical stability of APIs as well as the physical stability simultaneously, which is desirable during drug product development.

The composition strategy disclosed herein to control and/or reduce the formation of side products includes using a Lewis acid, controlling the pH, API form selection, selection of buffers, selection of stabilizers, process optimization, and combinations thereof.

Lewis Acids

A Lewis acid (electron-pair acceptor) can be used to stabilize an API. Lewis acids can include, but are not limited to $MgCl_2$ and $CaCl_2$). A Lewis acid can be used to promote re-closure of hydrolyzed lactone rings by stabilizing the electrophilic carbonyl-carbon. Thus, a Lewis acid can minimize side product composition by nucleophilic attack on a carbonyl bond. For example, $MgCl_2$ can be used to promote re-closure of lactone rings and prevent pilocarpine from hydrolyzing to pilocarpine acid.

Control of pH

The control of pH can include chemical control and physiochemical control.

Chemical aspect: Hydrolysis of a lactone ring is catalyzed by both acid and base and can be controlled by pH. Acid-catalyzed hydrolysis is relatively slower. Acids can catalyze the reaction making the carbonyl carbon more partially positive, by protonation of the carbonyl oxygen and therefore more susceptible for nucleophilic attack. Base-catalyzed hydrolysis is faster and generally not reversible. For example, a strong base, such as NaOH, can hydrolyze the lactone ring of pilocarpine and saponify it to pilocarpine acid salt. Once saponification occurs, this reaction is not reversible. To minimize this chemical degradation, the pH can be strictly controlled below the $pK_a$ of pilocarpine (about pH 6.5). In some embodiments, the pH can be controlled below 5.0, or below 4.0.

Physicochemical aspect: Physical appearance such as homogeneity and viscosity are two factors often considered during pharmaceutical product development process. A composition thickener, such as Carbopol® or Carbomer™, cannot function well to achieve desirable physical appearance or viscosity due to the protonation of the carbonyl group of acrylate or acrylic acid. To achieve desirable composition viscosity and maintain consistent physicochemical properties, the pH can be controlled above 3, or above about 4.0, or above about 5.0.

In some embodiments, compositions as described herein can have a pH of between about 3.0 and about 7.8, between about 5 and about 6, between about 4 and about 5, between about 4.5 and about 6, between about 4 and about 5.5, or between about 4.5 and about 5.5. In one embodiment, the pH is about 3.0-3.5. In one embodiment, the pH is about 4.2. In another embodiment, the pH is about 5.5.

API Selection

An API can be chosen from various salt forms, such as, a free base or different salt forms in an effort to increase chemical compatibility and minimize the chemical degradation. For example, pilocarpine free base or pilocarpine nitrate can be selected over pilocarpine HCl that has different solubility and/or crystallinity.

Buffer and Stabilizers

An API stabilizer can be used to form physical conjugates or complexes with the API that creates a steric hindrance to prevent or minimize API hydrolysis. The physicochemical interactions between the API and stabilizing agents includes, but is not limited to, hydrophobic interaction and hydrogen bonding. Several stabilizing agents that can be used in pilocarpine composition are included in Table 1. The selection of buffer or stabilizer depends on the working pH range of the drug product. The buffer can be used alone or in a buffer combination. The API stabilizer can be used alone or in a combination of stabilizers.

TABLE 1

List of preferred buffers and stabilizers

| Selection | Applicable Buffer (MW) | pKa | Effective Buffering Range |
|---|---|---|---|
| Buffer | Citrate buffer—pKa1 (192) | 3.13 | 2.2-5.0 |
|  | Citrate buffer—pKa2 (192) | 4.75 | 3.0-6.2 |
|  | Acetic acid/acetate buffer | 4.76 | 3.0-6.2 |
|  | Glycolic acid buffer (76) | 3.83 | 2.8-5.3 |
|  | Boric acid/borate buffer (62) | 9.14 | 8.0-10.0 |
| API Stabilizer | Lactic acid (90) | 3.86 | 2.8-5.3 |
|  | Ascorbic acid (176) | 4.70 | 3.3-6.2 |
|  | Azeliac acid (188.22) | 4.60 | 3.3-6.0 |

In some embodiments, a composition as described herein can have any combination of the above buffers/stabilizers. Compositions can include dual buffers, tri buffers, a quad buffer system and the like.

In some embodiments, a composition can include a citrate buffer and lactic acid. In some embodiments, a composition can include a citrate buffer and ascorbic acid. In some embodiments, a composition can include a citrate buffer and azeliac acid.

In some embodiments, a composition can include an acetic acid/acetate buffer and lactic acid. In some embodiments, a composition can include an acetic acid/acetate buffer and ascorbic acid. In some embodiments, a composition can include an acetic acid/acetate buffer and azeliac acid.

In some embodiments, a composition can include a glycolic acid buffer and lactic acid. In some embodiments, a composition can include a glycolic acid buffer and ascorbic acid. In some embodiments, a composition can include a glycolic acid buffer and azeliac acid.

In some embodiments, a composition can include a boric acid/borate buffer and lactic acid. In some embodiments, a composition can include a boric acid/borate buffer and ascorbic acid. In some embodiments, a composition can include a boric acid/borate buffer and azeliac acid.

In some embodiments, a composition can include a heterogeneous buffer containing sodium (or potassium, ammonium, or lithium) citrate and acrylic acid embedded in a polymer such as Carbomer™ or a cross-linked polyacrylic acid copolymer. In some embodiments, a composition can include a heterogeneous buffer containing an amino acid such as lysine and acrylic acid embedded in a polymer such as Carbomer™. In some embodiments, a composition can include a heterogeneous buffer containing histidine and acrylic acid embedded in a polymer such as Carbomer™.

In some embodiments, potassium ion or ammonium ion is preferred cation and chosen over sodium ion to prevent salting out at the same buffering capacity.

Process Optimization

In some embodiments, composition processes can have an impact (e.g., significant) on formation of impurities in the final product. A typical compounding process including mixing pilocarpine in aqueous medium, followed by mixing with other excipients can result in a high level of total impurities. However, depending on other variables described herein, typical compounding can result in a composition with acceptable amounts of impurity, in some embodiments.

Another compounding process can be using an oil dispersion approach. In some embodiments, composition preparation using an oil dispersion can result in a high level of total impurities. However, depending on other variables described herein, using an oil dispersion can result in a composition with acceptable amounts of impurity, in some embodiments.

A further formation process can include a post neutralization. In some embodiments, this post neutralization can control the total impurities. In some embodiments, the total impurities when using an oil dispersion is less than about 1%.

In some embodiments, a composition can include a pilocarpine free base, a citrate buffer, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, an acetic acid/acetate buffer, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, a glycolic acid buffer, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, a boric acid/borate buffer, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, lactic acid, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, ascorbic acid, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, azeliac acid, $MgCl_2$, and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, a citrate buffer, $CaCl_2$), and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, an acetic acid/acetate buffer, $CaCl_2$), $MgCl_2$ and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, a glycolic acid buffer, $CaCl_2$), and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, a boric acid/borate buffer, $CaCl_2$), and thickener(s). In some embodiments, the composition does not include a thickener. In some embodiments, the composition has a pH of between about 3.0 and 7.8. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, lactic acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, ascorbic acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include a pilocarpine free base, azeliac acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a citrate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, an acetic acid/acetate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a glycolic acid buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a boric acid/borate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, lactic acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, ascorbic acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, azeliac acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a citrate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, an acetic acid/acetate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a glycolic acid buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, a boric acid/borate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, lactic acid, $CaCl_2$), and thickener(s). In some embodiments, the composition does not include a thickener.

In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, ascorbic acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, azeliac acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a citrate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, an acetic acid/acetate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a glycolic acid buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a boric acid/borate buffer, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, lactic acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, ascorbic acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, azeliac acid, $MgCl_2$, and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a citrate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, an acetic acid/acetate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a glycolic acid buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, a boric acid/borate buffer, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, lactic acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, ascorbic acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine nitrate, azeliac acid, $CaCl_2$), and thickener(s). In some embodiments, the composition does not include a thickener. In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

In some embodiments, a composition can include pilocarpine HCl, lysine, $MgCl_2$, and thickener(s). In some embodiments, the composition does not include thickener(s). In some embodiments, the composition has a pH of between about 3.0 and 8.0. In some embodiments the pH is about 4.2. In other embodiments, the pH is about 5.5. This composition can be produced by standard processes of mixing pilocarpine in an aqueous medium, followed by mixing other excipients. In other embodiments, the composition can be produced in an oil phase dispersion approach. In still other embodiments, the composition can be produced using a post neutralization approach as described herein.

The compositions described can have a viscosity between about 2,000 cps and about 200,000 cps. In some embodiments, the viscosity is between about 2,000 cps and about 3,000 cps. In other embodiments, the viscosity is between about 60,000 cps and about 65,000 cps.

In some embodiments, the compositions described herein can be used in methods to treat ocular conditions. Ocular conditions can include, glaucoma, macular degeneration, dry eye, red eye, myopia, presbyopia, macular edema, ocular inflammation, surgical trauma, allergic conjunctivitis, viral conjunctivitis, bacterial conjunctivitis, blepharitis, anterior uveitis, protrusion of the eye; swelling of eye tissues, discharge, crusting or excessive tearing, eyelids stuck together, blood on the colored part or white of the eye, cataracts, corneal clouding, corneal ulcer, dystrophies, herpes simplex keratitis, keratoconus, pterygium, recurrent erosion syndrome, eye movement disorder, ocular tumor, enucleation, eyelid or orbit injuries, ectropion, Graves' disease, involuntary eyelid blinking, or a combination thereof.

Treating ocular compositions can be accomplished by injection to the eye or systemically, or topically in the form of drops, liquids, emulsions, particles, lotions, creams, oils, ointments, gels, or a combination thereof. Topically delivered can be to the surface of the eye or on or around the eye, such as but not limited to, the eyelid.

Administration of the herein described compositions can be multiple times daily, one daily, once weekly, once months, biannually, annually, or the like.

The compositions described herein can be incorporated into a kit. In some embodiments, a kit comprises a tube, a formulation described herein, and instructions for use. In other embodiments, a kit comprises a composition including pharmaceutical agents comprising ester and/or lactone ring structures, in sustained-release solid, semi-solid (gel, lotion, cream or ointment) formulations for topical and ophthalmic applications, a tube, and instructions for use.

In some embodiments, a kit comprises a composition including pharmaceutical agents comprising ester and/or lactone ring structures, in sustained-release solid, semi-solid (gel, lotion, cream or ointment) formulations for topical and ophthalmic applications packaged in a tube or the like, and instructions for use.

In some embodiments, instructions for use can comprise one or more of the following steps: 1. Wash your hands prior to applying the product around the eyes. 2. Break the tamper-evident seal and remove the cap from the tube. Do not use if the seal was broken before use. 3. Squeeze a quarter inch (approximately the same size as the length of the tip of the tube) of the ophthalmic topical cream (i.e., cream) from the tube in a straight line onto the fingertip. 4.

To apply the cream to upper and/or lower eyelids, gently apply (avoid dragging or rubbing) the cream back and forth across the lower part of the upper eyelid until the cream is fully applied. Avoid placing the cream directly from the tube to the eyelid, applying too close to your eyelashes or in the eye. 5. Repeat steps 3 and 4 for the other eye. 6. Place the cap securely back on the tube and store at room temperature. 7. Wash your hands after the product has been applied to both eyes. 8. The ophthalmic topical cream needs to be applied on the upper eyelids of both eyes BID in the morning (8 AM±2 hours) and in the evening (8 PM±2 hours). Steps can be added or removed, or can occur in a different sequence.

In some embodiments, instructions for use can further comprise the following tips: 1. Small droplets of condensation may release from the tube when squeezed. 2. Don't let the tip of the tube touch the eye, hands or any other surfaces to keep it free from contamination. 3. Please refrain from wearing contact lenses or using artificial tears/ocular lubricants, and forgo the use of eye makeup, including but not limited to eye shadow, eye creams/lotions/gels/serums, eyelash extensions, false eyelashes, or other eye products during the study. 4. Refrain from direct sunlight for 30 minutes after application of the cream. It is recommended to wear sunglasses that block ultraviolet A and B (UVA and UVB) light when outside in direct sunlight. Tips can be added or removed, or can be presented in a different sequence.

In other embodiments, a kit can further include a buffer, a stabilizer, or a combination thereof as described herein.

In some embodiments, a kit is described comprising a tube comprising a sustained-release solid, semi-solid cream, lotion or ointment formulation used for ophthalmic therapy to be dosed on or around the eye, and eye-lid including: a pharmaceutical agent including an ester, a lactone ring, or an ester and a lactone ring, and instructions for use. The kit can further comprise a buffer, a stabilizer, or a combination thereof. The kit can comprise a formulation that has a pH of between about 3.0 and 8.0.

The compositions described herein can be applied to the upper and/or lower eyelid(s). In some embodiments, a user can dispense a dosage of a cream described herein onto the fingertip to apply to the upper and/or lower parts of the eyelid(s). A dosage can be equivalent to a quarter inch which is approximately the same size as the length of the tip of the tube in which the cream is packaged.

Example 1

Chemical instability of compositions is demonstrated from experimental results by formation of impurities as shown in FIG. 1. Formulations are compounded with/by the same formulations, equipment/processes and stored at controlled room temperature or 40° C. The difference between formulations is a difference in formulation pH: one at pH 3.5 and one at pH 5.0.

At controlled room temperature, the total impurities level is found to be about 50% more when comparing the formulation at pH 5.0 to that at pH 3.5. While at 40° C., the total impurities level is found even more than 100% when comparing the formulation at pH 5.0 to that at pH 3.5. It should be noted that, at two-month time point, the total impurities level of the formulation at pH 5.0 and stored at controlled room temperature exceeds that of the formulation at pH 3.5 and stored at 40° C.

On the other hand, the viscosity for Formulation #1 at a pH of 3.5 is found to be 5,100 cps which fails to meet desirable physical criteria, while Formulation #2 at pH 5.0 is 128,100 cps which is more desirable for most dermal product applications. The test results are summarized in Table 2.

TABLE 2

Viscosity values of the formulation at two different pH

| Formulation # | Formulation pH | Formulation viscosity (cps) |
|---|---|---|
| 1 | 3.5 | 5,100 |
| 2 | 5.0 | 128,100 |

Example 2

Figure 2:
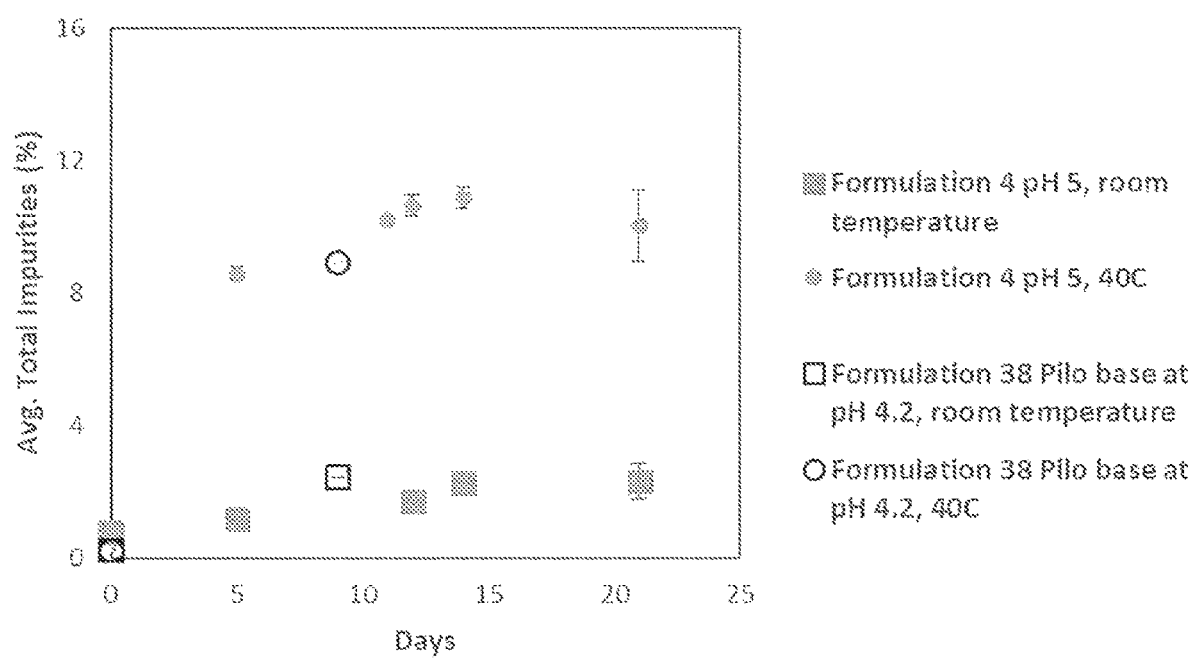
FIG. 2. Average total impurities (%) of Formulations 4 and 38 that were compounded with/by the same compositions, equipment, and processes. (■) represents Formulation 4 formulated with Pilocarpine HCl at pH 5.0 and stored at controlled room temperature, (●) represents Formulation 4 formulated with Pilocarpine HCl at pH 5.0 and stored at 40° C./75% RH, (□) represents Formulation 38 formulated with Pilocarpine free base at pH 4.2 and stored at controlled room temperature, and (○) represents Formulation 38 formulated with Pilocarpine free base at pH 4.2 and stored at 40° C./75% RH. There were n=3 at each sampling time points.

An experiment is run to show differences in total impurities levels when formulations include pilocarpine HCl or pilocarpine free base. The test results of total impurities of the formulation compounded with pilocarpine free base at pH 4.2 (Formulation #38) are shown in FIG. 2. For comparison, the same formulations are compounded with the same equipment, and processes except with pilocarpine HCl, and the test results of total impurities of the formulation (Formulation #4) are included in FIG. 2. Between Formulations #4 and #38, a similar total impurities level is found when the formulations are stored at room temperature, while a lower level of total impurities found for Formulation #38, due to the combination effect of pH and pilocarpine free base.

The viscosities of these two formulations are found comparable. The viscosity for Formulation #4 at a pH of 5.0 is determined to be 72,700 cps, while that for Formulation #38 at pH 5.5 is 60,520 cps. The test results are summarized in Table 3.

TABLE 3

Formulation viscosity of Formulation #4 and Formulation #38 at different pH.

| Formulation # | Formulation pH | Formulation viscosity (cps) |
|---|---|---|
| 4 | 5.0 | 72,700 |
| 38 | 5.5 | 60,520 |

Example 3

The following experiment discloses the findings in total impurity levels when a formulation is compounded with an aqueous medium of water or a citrate buffer.

Figure 3:
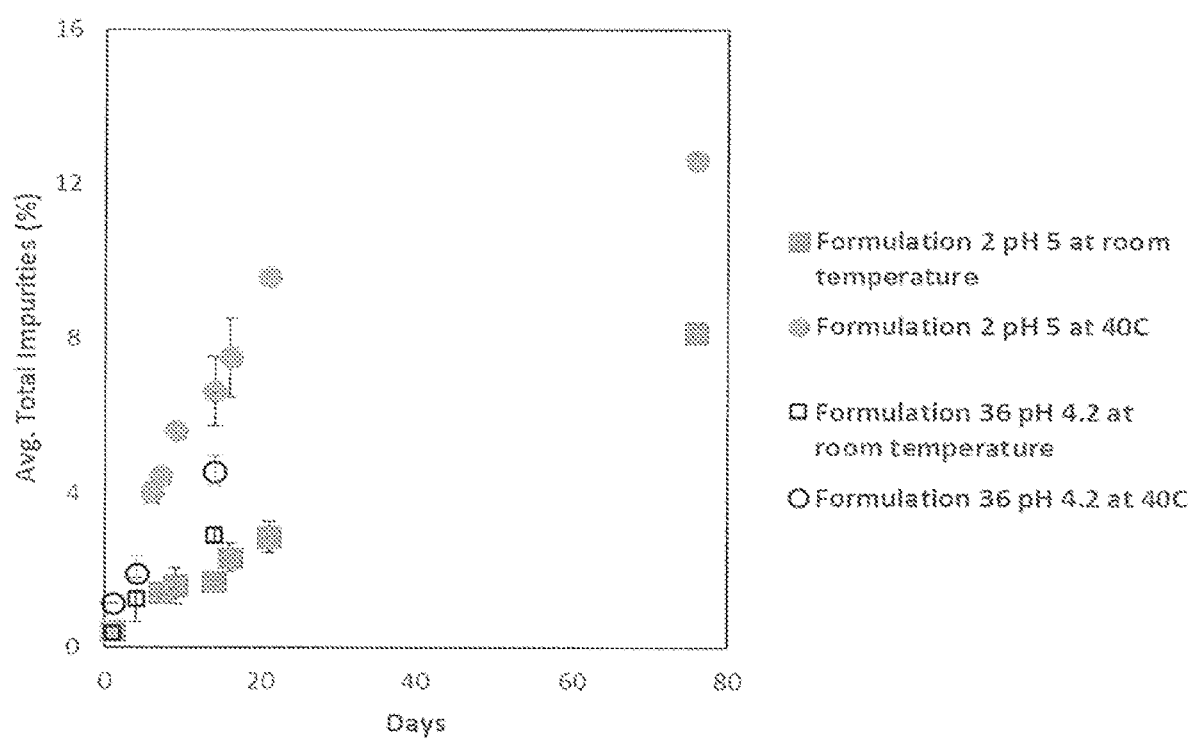
FIG. 3: Average total impurities (%) of Formulations 2 and 36 that were compounded with/by the same compositions, equipment, and processes, except the aqueous media. (■) represents Formulation 2 formulated with Pilocarpine HCl at pH 5.0 with water and stored at controlled room temperature, (●) represents Formulation 2 formulated with Pilocarpine HCl at pH 5.0 with water and stored at 40° C./75% RH, (□) represents Formulation 36 formulated with Pilocarpine HCl at pH 4.2 with citrate buffer and stored at controlled room temperature, and (○) represents Formulation 36 formulated with Pilocarpine HCl at pH 4.2 with citrate buffer and stored at 40° C./75% RH. There were n=3 at each sampling time points.

Test results of total impurities of the formulation compounded with pilocarpine HCl at pH 4.2 with a 10 mM to 100 mM as shown in FIG. 3. For comparison, the same formulations are compounded with the same equipment and processes except using water as the aqueous media, and the test results of total impurities of the formulation (Formulation #2) are included in FIG. 3. Between Formulations #2 and #36, a similar total impurities level is found when the formulations are stored at room temperature, while a lower level of total impurities is found for Formulation #36, due to the combination effect of pH and the aqueous medium of buffer.

On the other hand, the viscosity for Formulation #2 at a pH of 5.0 is found to be 128,100 cps that is able to meet desirable physical criteria but fails to meet chemical stability criteria as described above, while that for Formulation #36 at pH 4.2 is 2,358 cps which is less desirable for physical criteria but favorable for chemical stability. The viscosity test results are summarized in Table 4.

TABLE 4

Formulation viscosity of Formulation #2 and Formulation #36 at different pH.

| Formulation # | Formulation pH | Formulation viscosity (cps) |
|---|---|---|
| 2 | 5.0 | 128,100 |
| 36 | 4.2 | 2,358 |

Example 4

Pilocarpine formulations are formed using the processes as outlined in Table 5.

TABLE 5

Summary of test results when formulation was compounded with various processes

| Process | Condition | pH | Pilocarpic Acid (%) | Isopilocarpic Acid (%) | Isopilocarpine (%) | Total Impurities (%) |
|---|---|---|---|---|---|---|
| Standard Process | Unsterilized | 5.45 | 1.14 | 0.08 | 2.01 | 7.17 |
| Oil Phase Dispersion | Unsterilized | 5.40 | 1.73 | 0.34 | 2.9 | 9.82 |
| Post Neutralization | Unsterilized | 5.29 | 0.09 | 0.09 | 0.14 | 0.62 |

Figure 4:
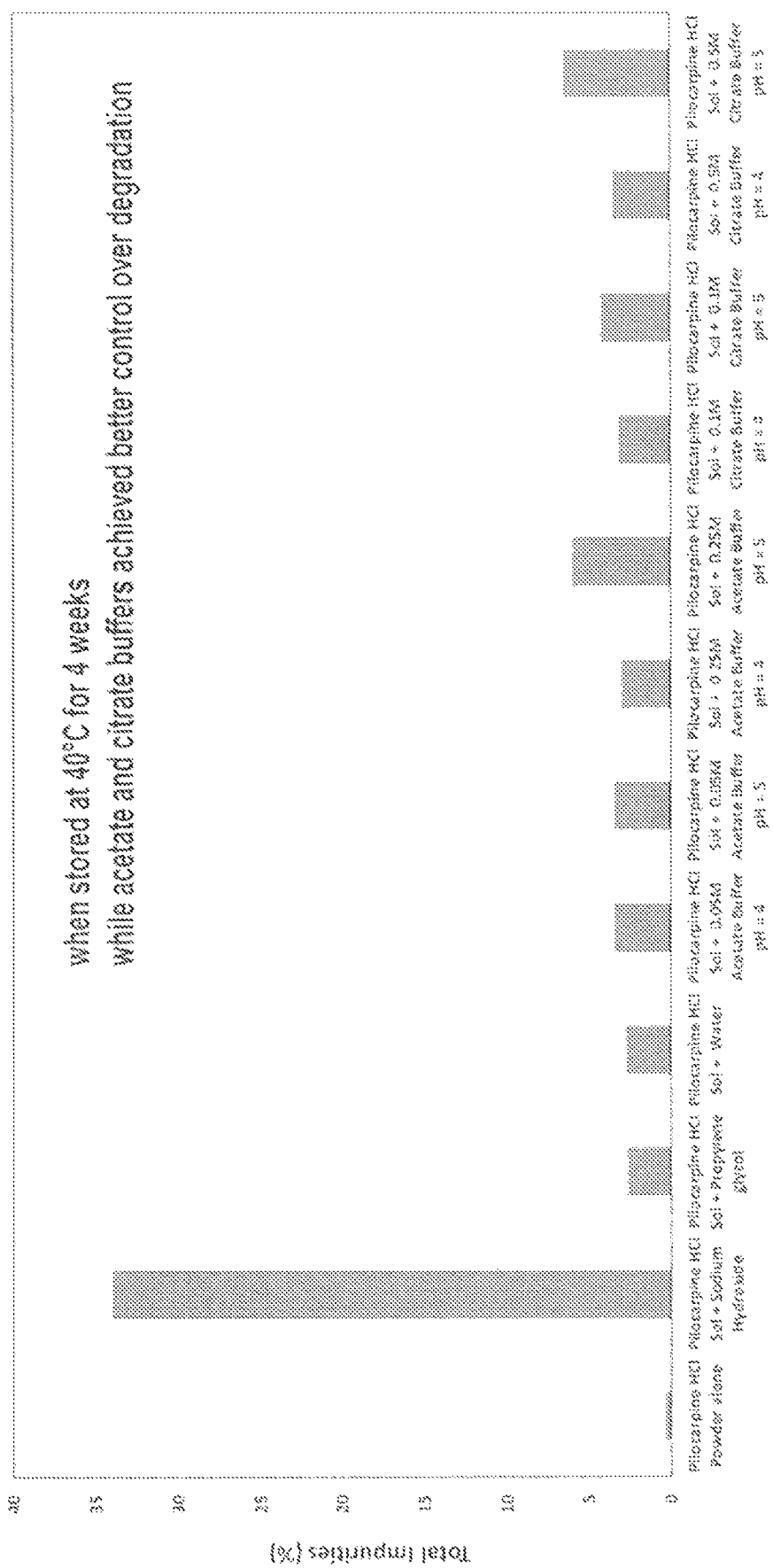
FIG. 4: Impurity level of Pilocarpine when incubating with various media.

The results demonstrate that use of strong base, such as sodium hydroxide, can have a significant impact on API stability. Results are shown in FIG. 4. The local high pH in a micro environment of a semi-solid dosage formulation can trigger the degradation process, resulting in an excessive impurity level.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A sustained-release solid, semi-solid cream, lotion or ointment formulation used for ophthalmic therapy to be dosed on or around the eye, and eye-lid including:
   pilocarpine
   a citrate buffer, a stabilizer, or a combination thereof; and
   a Lewis acid,
   wherein the Lewis acid is $MgCl_2$ or $CaCl_2$, and
   wherein the formulation is at a pH of 3.5 to 5.5 and at a viscosity range of 60,000 cps to 128,100 cps.

2. The formulation of claim 1, wherein the stabilizer is lactic acid, ascorbic acid, azeliac acid, or a combination thereof.

3. The formulation of claim 1, further including a thickener or thickeners.

4. The formulation of claim 1, in an aqueous medium.

5. The formulation of claim 1, wherein the pH is 3.5.

6. The formulation of claim 1, wherein the pH is 4.2.

7. The formulation of claim 1, formed using a post neutralization process.

8. The formulation of claim 1, wherein the desirable physical and chemical stabilities are achieved even at a lower pH such as 3.5 to provide a sustained release in topical ophthalmic usage.

9. The formulation of claim 1, wherein the desirable physical and chemical stabilities provide a consistency for topical and ophthalmic semi-solid dosage forms.

10. The formulation of claim 1, wherein the pH is 5.5.

11. A sustained-release solid, semi-solid cream, lotion or ointment formulation used for ophthalmic therapy to be dosed on or around the eye, and eye-lid including:
  pilocarpine
  a buffer, a stabilizer, or a combination thereof; and
  a Lewis acid,
  wherein the Lewis acid is $MgCl_2$ or $CaCl_2$, and
  wherein the formulation is at a pH of 3.5 to 5.5 and at a viscosity range of 60,000 cps to 128,100 cps.

* * * * *